United States Patent [19]
Goldstein

[11] Patent Number: 5,910,479
[45] Date of Patent: Jun. 8, 1999

[54] **METHOD FOR THE TREATMENT OF *STREPTOCOCCUS PNEUMONIAE* INFECTION**

[75] Inventor: Beth P. Goldstein, Tarrytown, N.Y.

[73] Assignee: AMBI Inc., Tarrytown, N.Y.

[21] Appl. No.: 08/771,244

[22] Filed: Dec. 20, 1996

Related U.S. Application Data

[60] Provisional application No. 60/028,812, Oct. 18, 1996.

[51] Int. Cl.$^6$ ................................................ A61K 38/16
[52] U.S. Cl. ................................. 514/9; 514/12; 514/13
[58] Field of Search .................................. 514/9, 11, 12, 514/13; 530/317, 324, 325, 326, 825

[56] References Cited

U.S. PATENT DOCUMENTS

| | | | |
|---|---|---|---|
| 4,548,924 | 10/1985 | Michel | 514/10 |
| 4,931,390 | 6/1990 | Recsei | 435/69.1 |
| 4,980,163 | 12/1990 | Blackburn et al. | 514/2 |
| 5,112,806 | 5/1992 | Chatterjee et al. | 514/9 |
| 5,217,950 | 6/1993 | Blackburn et al. | 514/2 |
| 5,231,013 | 7/1993 | Jung et al. | 435/71.3 |
| 5,260,271 | 11/1993 | Blackburn et al. | 514/2 |
| 5,310,900 | 5/1994 | Barriere et al. | 540/455 |
| 5,334,582 | 8/1994 | Blackburn et al. | 514/2 |
| 5,512,269 | 4/1996 | Molina y Vedia | 424/45 |
| 5,637,565 | 6/1997 | Anger et al. | 514/11 |
| 5,650,320 | 7/1997 | Caufield et al. | 435/252.3 |

FOREIGN PATENT DOCUMENTS

| | | |
|---|---|---|
| 0362520 | 4/1990 | European Pat. Off. . |
| 9428726 | 12/1994 | WIPO . |

OTHER PUBLICATIONS

Bottone et al, Characteristics of a Bacteriocin Derived from . . . Applied Microbiology. vol. 22, No. 2, pp. 200–204, Aug. 1971.
Niu, et al., Antimicrob. Agents Chemother. 35: 998–1000 (1991).
Chatterjee, et al., J. Antibiot. (Japan) 45(6): 839–845 (1992).
Reisinger, et al., Arch. Microbiol. 127: 187–198 (1992).
Bierbaum et al. Cloning, Sequencing, and production of . . . FEMS Microbiology Lett. vol. 127, pp. 121–126, 1995.
Malabarba et al. Synthesis and Biological Activity of . . . J. Antibiotics, vol. XLIII, No. 9, pp. 1089–1097, Sep. 1990.
Brotz et al. The Lantibiotic mersacidin inhibits . . . Eur. J. Biochem. vol. 246, pp. 193–199, 1997.
Brotz et al. The lantibiotic mersacidin inhibits . . . Antimicrob. Agents Chemotherapy. vol. 42, No. 1, pp. 154–160, Jan. 1998.
Sahl et al. Biosynthesis and biological activities . . . Eur. J. Biochem. vol. 230, pp. 827–853, 1995.
Orberg, et al., Applied Environ. Microbiol. 49:538–542 (1985).
Brotz, et al., Antimicrob. Agents Chemotherapy 39(3): 714–719, (1995).
Barrett, et al., Diagn. Microbiol. Infect. Dis. 15(7): 641–644, (1992).
Murray, B.E., Clin. Micorbiol. Rev. 3(1): 46–65 (1990).
"Invasive Group A Streptococcal Infections —United Kingdom, 1994" MMWR, pp. 401–402 (1994).
Bavin, et al., Lancet 1:127–129 (1952).
Gowans, et al., Brit. J. Pharmacol. 7:438–449 (1952).
Szybalski, W., Dept. Health and Human Services, FDA Fed. Regis. 53 (66): pp. 1095–1103 (1988).
Hirsch, et al., Lancet ii:190–193 (1949).
Mattick, et al., Lancet 2:5–8 (1947).
Somma, et al., Antimicrob. Ag. Chemother. 11:396–401 (1977).
Arioli, et al., J. Antibiot. 29:511–515 (1976).
Karchmer, A.W., Ann. Int. Med. 115(9):739–741 (1991).
Jung, "Nisin and Novel Lantibiotics," ESCOM Science Publishers, Leiden, pp. 1–34 (1991).
Emori, et al., Clin. Microbiol. Rev. 6(4):428–442 (1993).
Ramseier, H.R., Archiv. für Mikrobiol. 37:57–94 (1960).
Hossack, et al., Federal Register, vol. 53, No. 668, pp. 1–30, Apr. 6, 1988.
Stutman, H.R., Infections in Medicine 10: Suppl. D.:51–55 (1993).
Thornsberry, et al., Infections in Medicine 10 Suppl. D.: 15–24 (1993).
Noble, et al., FEMS Microbiol. Lett. 72:195–198 (1992).

*Primary Examiner*—Jeffrey E. Russel
*Attorney, Agent, or Firm*—White & Case L.L.P.

[57] ABSTRACT

The invention concerns methods for killing antibiotic-resistant pathogenic bacteria which cause disease in humans and animals. In particular, the methods are directed to the killing of antibiotic-resistant or multi-drug resistant *Streptococcus pneumoniae* bacterial strains. The methods employ a lanthocin such as nisin or a variant thereof as bactericidal agent.

6 Claims, No Drawings

METHOD FOR THE TREATMENT OF *STREPTOCOCCUS PNEUMONIAE* INFECTION

CROSS-REFERENCE TO RELATED APPLICATIONS

This application claims the benefit, under 35 U.S.C. § 119(e), of U.S. Provisional Patent Application No. 60/028812, filed on Oct. 18, 1996.

BACKGROUND OF THE INVENTION

Nisin is a bacteriocin, an antimicrobial substance produced by a food grade organism and is a member of a group of similar substances referred to as lantibiotics (or lanthocins herein) and which, among others, include subtilin, epidermin, gallidermin, pep 5, cinnamycin, duramycin and ancovenin.

Nisin is produced by *Lactococcus lactis* subsp. *lactis* belonging to the Lancefield serological group N [Mattick, A. T. R. and A. Hirsch, 1947 Lancet. 2, 5]. Nisin is a peptide comprised of 34 amino acid residues and contains five ring structures cross-linked by thioether bridges that form lanthionine or β-methyllanthionine. These thioethers result from the condensation of cysteine sulfhydryl groups with dehydro side chains formed from either serine or threonine residues as a result of posttranslational modifications of a nisin precursor peptide.

It has been reported that nisin acts as a cationic surface active agent and that its activity can be neutralized by anionic detergents [Ramseier, H. R. 1960 Arch. Mikrobiol, 37, 57], and at a molecular level that nisin acts at the cytoplasmic membrane and inhibits peptidoglycan biosynthesis [Reisinger et al. 1980 Arch. Microbiol. 127, 187]. The action of nisin against vegetative bacteria is most likely the result of voltage dependent depolarization of the plasma membrane following insertion of the peptide into the lipid bilayer, possibly through the interaction of adjacent nisin molecules to form a transient pore or channel. The molecular properties of nisin and the mechanism of its biosynthesis have been the subject of extensive recent reviews [Jung, G. and H. -G. Sahl 1991 Nisin and Novel Antibiotics ESCOM Science Publishers, Leiden].

Nisin is considered to have a narrow spectrum of activity and generally is only active against certain Gram positive bacteria, except when combined with a chelating agent when nisin is surprisingly active against Gram negative bacteria and exhibits enhanced activity against Gram positive bacteria (U.S. Pat. Nos. 5,135,910; 5,217,950; and 5,260,271 to Blackburn, et al.). Nisin has been used as an antimicrobial food preservative and is accepted as safe by JEFCA and various national authorities regulating the use of food additives including those of the USA, UK and EEC.

SUMMARY OF THE INVENTION

The invention concerns methods for preventing and treating diseases attributable to infection by antibiotic-resistant or multidrug-resistant bacterial pathogens. The inventive methods may suitably be used, among others, against antibiotic-resistant bacterial strains of the genus Streptococcus. In particular, the invention concerns methods for preventing and treating antibiotic-resistant or multidrug-resistant bacteria of the species, *Streptococcus pneumoniae*, commonly known as "pneumococcus," with nisin at very low, non-toxic concentrations.

Bacterial infections to be treated within the scope of the invention, and which are caused by *S. pneumoniae* include, pneumococcal meningitis, bacteremia, pneumonia, otitis media and the like. The methods employ nisin and other lanthionine-containing bacteriocins (lanthocins), as well as structural variants thereof produced by genetic engineering or semisynthetic chemistry.

DETAILED DESCRIPTION OF THE INVENTION

Bacterial infections, particularly those acquired in hospitals have become more difficult to treat, in part, as the result of the selection of clinical isolates resistant to those antibiotics currently used for therapy. In addition, β-lactam-antibiotic-resistant and multidrug-resistant strains of *Streptococcus pneumoniae* are among the bacterial strains that epitomize the problem. *Streptococcus pneumoniae* (previously known as *Diplococcus pneumoniae*, and also frequently referred to as "pneumococcus"), a Gram-positive bacterium, is a leading cause of illness and death in the United States and worldwide. In the U.S., *S. pneumoniae* is responsible for causing approximately 3,000 cases of meningitis, 50,000 cases of bacteremia, 500,000 cases of pneumonia and 7,000,000 cases of otitis media each year (Centers for Disease Control and Prevention, MMWR 1996; 45 (No. RR-1): 1–2).

Although the disease clinically defined as "pneumonia" may be caused by a variety of organisms, it is principally caused (particularly among normally healthy individuals in the community) by *Streptococcus pneumoniae*. *Streptococcus pneumoniae* is also responsible for the majority of cases of otitis media (both acute and chronic) in children and, particularly since the advent of widespread immunization of children against *Haemophilus influenzae*, is the major cause of meningitis in this age group, at least in developed countries (Centers for Disease Control and Prevention, Ibid and J. O. Klein, APUA Newsletter 14(2): 1–4, 1996).

Whereas immunization against *Streptococcus pneumoniae* is now recommended for the elderly, it is still underutilized. Currently available vaccines are not effective in eliciting the desired response in children under two years of age. (Centers for Disease Control and Prevention, Ibid).

Traditionally, pneumococcal disease has been treated with penicillin or erythromycin, although cephalosporins and the newer macrolides are increasingly being used. However, penicillin-resistant and multidrug-resistant strains are emerging in the U.S. and are widespread in some areas (Center for Disease Control, Ibid and J. O. Klein, Ibid). Furthermore, highly toxigenic strains of Group A streptococci [Anonymous 1994 Morbidity Mortality Weekly Report 43: 401] are difficult to treat and frequently result in the rapid demise of the patient. It is clear that new antimicrobial agents that are active against multiply resistant bacteria or that are more effective and more rapidly acting are needed to combat these infections.

As disclosed in copending U.S. application Ser. No. 08/667,650, nisin has previously been shown to be a potent bactericidal agent in vitro against pathogenic strains of Gram positive bacteria, including multidrug-resistant pneumococci. Although, in principle, nisin might be considered for use in certain situations wherein antimicrobials are called for and the bacteriocin was shown to be effective in preliminary animal model studies [Mattick, A. T. R. and A. Hirsch, 1947 Lancet. 2, 5; Bavin, E. M., et al 1952 Lancet 1: 127; Gowans, J. L., et al 1952 Brit. J. Pharmacol. 7: 438; Hirsch, A. and A. T. R. Mattick 1949 Lancet ii: 190], nisin was found to be insufficiently useful to be developed therapeutically in human or veterinary medicine. However, the present invention is based on our finding that nisin has potent activity against pneumococcal infection in animals at surprisingly low doses and the finding that, unexpectedly, nisin has excellent activity against such infection when administered subcutaneously.

It is also known in the prior art that certain strains of pneumococci are particularly virulent in infection model studies in mice. In fact, very low bacterial inocula of these strains of S. pneumoniae are needed to produce lethal infections in mice, as compared with virulent strains of other bacterial species, such as Staphylococcus aureus. Additionally, it is usually observed that higher doses of antimicrobial agents are needed in mice to cure or prevent infections caused by such virulent strains of S. pneumoniae than would be expected on the basis of the in vitro activities of antimicrobial agents. In particular, experiments have shown that higher dosages of an antimicrobial are needed to cure acute S. pneumoniae infections than to cure acute S. aureus infections in mice, even when the antimicrobial agent is significantly more active against S. pneumoniae than against S. aureus in vitro. For example, in a recent publication regarding glycopeptide antibiotics, ratios of 50% effective doses in mice (in mg/kg total dose) to minimal inhibitory concentration (MIC) in vitro (in ug/ml) varied from 0.4 to 2 for S. aureus and from 3.6 to 25 for S. pneumoniae (Goldstein et al., Antimicrob. Agents Chemother. 39: 1580–1588, 1995).

Our experiments show that in the acute mouse infection model, nisin was unexpectedly more active against a highly virulent strain of S. pneumoniae than against S. aureus.

It has also been reported in the prior art that whereas nisin was efficacious against S. aureus and Streptococcus pyogenes infections in animals when administered by the intravenous (i.v.) or intraperitoneal (i.p.) routes, nisin had no or poor efficacy when administered subcutaneously (s.c.). (Hirsch et al. Lancet ii: 190–193, 1949 and Bavin et al. Lancet i: 127–129, 1952). According to the authors, little or no nisin was absorbed into the blood stream upon s.c. administration, the bulk of the drug remaining at the site of injection in rabbits (Bavin et al., Ibid). Some nisin absorption was observed after intramuscular (i.m.) injection, but no efficacy data were presented for this route of administration (Bavin et al. Ibid). By the i.p. route of administration, nisin was reported to be as active as penicillin as an antimicrobial agent (Bavin, et al., Ibid.).

Our experiments show that nisin was unexpectedly and surprisingly highly active in the S. pneumoniae infection model in mice, when administered subcutaneously. Furthermore, we have observed that when given i.v., nisin was actually more active than either penicillin or vancomycin. We have further shown that nisin analogs are active in the mouse model when administered intravenously.

These findings demonstrate that not only nisin, but other related members of this class of lanthocin antimicrobial peptides, including structural variants of these molecules produced by genetic engineering or by semisynthetic chemistry, should be useful in the prevention or therapy of infections caused by pneumococci in humans and animals. The fact that nisin is efficacious when administered by a route other than i.v. makes treatment of community-acquired infections feasible.

Effective pharmaceutical formulations of these peptides include simple aqueous solutions suitable for parenteral delivery of the active agent via intravenous (i.v), intramuscular (i.m.), subcutaneous (s.c.), intranasal, intrathecal or intraperitoneal (i.p.) routes so as to permit blood and tissue levels in excess of the minimal inhibitory concentration (MIC) of the active agent to be attained and thus to effect a reduction in bacterial titers in order to prevent, cure or alleviate an infection. Furthermore, it is anticipated that the lanthocin antimicrobial agent could be co-administered, at the same time or consecutively, with other antimicrobial agents so as to more effectively provide for a broader spectrum therapy, especially useful, in the absence of a specific diagnosis prior to initiating therapy.

These findings demonstrate that not only nisin, but other related members of this class of lanthocin antimicrobial peptides, including subtilin; epidermin; gallidermin; pep 5; cinnamycin; duramycin and ancovenin, as well as structural variants of these molecules produced by genetic engineering or by semisynthetic chemistry, should be useful in the prevention or therapy of infections caused by antibiotic-resistant bacteria in humans and animals.

EXAMPLE 1

Bacterial strains. Streptococcus pneumoniae Felton and Staphylococcus aureus Smith were used in vitro and in infection experiments.

Minimal inhibitory concentration (MIC). MIC were determined using broth microdilution methodology, as previously described (National Committee for Clinical Laboratory Standards, 1990. Approved Standard M7-A2. Methods for dilution antimicrobial susceptibility tests for bacteria that grow aerobically. 2nd ed. National Committee for Clinical Laboratory Standards, Villanova, Pa.). Cation-adjusted Mueller-Hinton broth was used; for S. pneumoniae, the medium was supplemented with 5% fetal bovine serum. Bovine serum albumin (0.02%); final concentration 0.01%) was used in the diluent to prevent sticking of nisin to plastic microtiter wells.

In various experiments, the MIC of nisin for S. aureus Smith varied between 1 and 2 $\mu$g/ml, whereas the MIC for S. pneumoniae Felton varied between 0.06 and 0.25 $\mu$g/ml.

Mouse i.p. infection model. Staphylococcus aureus Smith was grown in veal infusion broth and each mouse was infected intraperitoneally with $10^6$ colony-forming units (CFU), diluted in broth containing 5% (w/v) Difco bacteriological mucin. Streptococcus pneumoniae Felton strain was grown in Difco Brain Heart Infusion broth (BHI) and each mouse was infected intraperitoneally with $10^3$ CFU, diluted in BHI. Mice were divided into groups of 5. One group of 5 mice did not receive any treatment and served as control. Other groups of mice received different dosages of nisin. Nisin was administered either intravenously (via the tail vein in. 0.1 ml of 5% dextrose for injection) or subcutaneously (in 0.2 ml). Two injections were given to each mouse, the first within 10 minutes after infection and the second after 5 hours. The mice were observed for 5 days in order to record deaths or adverse signs. Different dosages of vancomycin or penicillin were administered i.v. in 0.1 ml of 5% glucose for injection.

EXAMPLE 2

Efficacy of nisin against S. aureus infection in mice.

These experiments were conducted as described in Example 1 above. The results are shown in Table 1 below.

TABLE 1

Efficacy of iv nisin against S. aureus septicemia in mice

| Treatment regimen (i.v.)* | % survival |
| --- | --- |
| No treatment | 0 |
| 20 mg/kg, once | 50 |
| 10 mg/kg, once | 17 |
| 10 mg/kg, twice | 100 |
| 5 mg/kg, twice | 83 |

*Mice were injected intravenously within 10 minutes after infection; in some cases a second injection was administered 5 hours after infection. Anti-infective agents administered in 0.1 ml/mouse/treatment of 5% dextrose for injection.

As shown in Table 1, nisin administered i.v. was 100% efficacious in preventing the death of mice at a dosage of 10 mg/kg/injection. The dosage of 5 mg/kg/injection was slightly less efficacious (83%).

EXAMPLE 3

Efficacy of nisin i.v. against *S. pneumoniae* infection in mice.

These experiments were conducted as described in Example 2 above. The results are shown in Tables 2a, 2b, 2c and 2d below.

TABLE 2a

Efficacy of i.v. nisin against *Streptococcus pneumoniae*

| Inoculum (CFU/mouse) | Treatment (mg/kg/dose)* | Survivors/total | (%) |
|---|---|---|---|
| $1 \times 10^2$ | 0 | 0/5 | 0 |
| $1 \times 10^3$ | 0 | 0/5 | 0 |
| $1 \times 10^3$ | 1.25 | 5/5 | 100 |
| $1 \times 10^3$ | 2.5 | 5/5 | 100 |
| $1 \times 10^3$ | 5 | 5/5 | 100 |
| $1 \times 10^3$ | 10 | 5/5 | 100 |

*Mice were injected intravenously, once within 10 minutes after and once 5 h after infection. Anti-infective agents were administered in 0.1 ml/mouse/treatment of 5% dextrose for injection.

TABLE 2b

Efficacy of i.v. penicillin against *Streptococcus pneumoniae*

| Treatment (mg/kg/dose)* | Survivors | (%) |
|---|---|---|
| 0 | 0/5 | 0 |
| 0.5 | 0/5 | 0 |
| 1 | 1/5 | 20 |
| 2 | 1/5 | 20 |
| 4 | 3/5 | 60 |
| 8 | 1/5 | 20 |
| 16 | 4/5 | 80 |

*Mice were injected intravenously, once within 10 minutes after and once 5 h after infection. Anti-infective agents were administered in 0.1 ml/mouse/treatment of 5% dextrose for injection.

TABLE 2c

Efficacy of i.v. vancomycin against *Streptococcus pneumoniae*

| Treatment (mg/kg/dose)* | Survivors/total | (%) |
|---|---|---|
| 0 | 0/5 | 0 |
| 1 | 2/5 | 40 |
| 2 | 3/5 | 60 |
| 4 | 4/5 | 80 |
| 8 | 5/5 | 100 |
| 16 | 5/5 | 100 |
| 32 | 5/5 | 100 |

*Mice were injected intravenously, once within 10 minutes after and once 5 h after infection. Anti-infective agents were administered in 0.1 ml/mouse/treatment of 5% dextrose for injection.

As shown in Table 2a, nisin, administered i.v., was 100% efficacious in preventing the death of mice at the lowest dosage tested (1.25 mg/kg/injection). As shown in Tables 2b and 2c, penicillin and vancomycin, compounds normally used to treat Gram-positive infections, were less efficacious than nisin in the mouse infection model. It has been reported that the strain of *S. pneumoniae* used is fully susceptible to both antibiotics: the MICs of penicillin and vancomycin are, respectively, 0.016 and 0.5 µg/ml (Goldstein et al. Ibid).

Because the lowest dosage of nisin tested in the experiment of Table 2a protected 100% of infected mice, additional tests were conducted using lower dosages.

TABLE 2d

Efficacy of low-dose i.v. nisin against *Streptococcus pneumoniae*.

| Nisin (mg/kg/dose)* | Survivors/total | (%) |
|---|---|---|
| 0 | 1/6 | 17 |
| 0.078 | 6/6 | 100 |
| 0.156 | 6/6 | 100 |
| 0.312 | 6/6 | 100 |
| 0.625 | 6/6 | 100 |

*Mice were injected intravenously, once within 10 minutes after and once 5 hours after infection. Anti-infective agents were administered in 0.1 ml/mouse/treatment of 5% dextrose for injection.

As can be seen from Table 2d, dosages as low as 0.078 mg/kg/dose protected 100% of infected mice.

EXAMPLE 4

Efficacy of variant nisin molecules, containing amino acid substitutions, against bacterial infection in mice.

Bacterial infection and treatment studies were conducted as described in the previous examples, except that, where indicated, variant molecules were substituted for nisin in the treatment regimens. The two variant molecules tested here were: His27Lys, in which the histidine normally present in the nisin molecule at position 27 of the mature nisin peptide has been replaced by a lysine; His27Lys-His31Lys, in which two histidine residues normally present in the nisin molecule, at positions 27 and 31 of the mature peptide, have been replaced by lysines. These amino acid substitutions were introduced by means of codon changes engineered in the nisA gene, which encodes the primary structure of the peptide (Kuipers, et al., 1996, Antonie Van Leeuwenhoek 69: 161–169; Rollema, et al., 1995, Appl. Environ. Microbiol. 61: 2873–2878; Kuipers, et al., 1992, J. Biol. Chem. 267: 24340–24346; U.S. Pat. No. 5,516,682 to Hansen).

TABLE 3a

Efficacy of a variant nisin molecule, His27Lys, against *Staphylococcus aureus* septicemia in mice

| His27Lys (mg/kg/dose)* | Survivors/total | (%) |
|---|---|---|
| 0 | 0/6 | 0 |
| 5 | 6/8 | 75 |
| 10 | 8/8 | 100 |

*Mice were injected intravenously, once within 10 minutes after and once 5 hours after infection. Anti-infective agents were administered in 0.1 ml/mouse/treatment of 5% dextrose for injection.

As can be seen from Table 3a, dosages of 5 and 10 mg/kg/dose of a nisin variant, which contained lysine at position 27 of the mature peptide, protected 75 and 100% of infected mice, respectively, against *Staphylococcus aureus* infection. This is very similar to what occurred using the same dosages of nisin.

TABLE 3b

Efficacy of a variant nisin molecule, His27Lys,
against *Streptococcus pneumoniae* septicemia in mice

| His27Lys (mg/kg/dose)* | Survivors/total | (%) |
|---|---|---|
| 0 | 0/6 | 0 |
| 1.25 | 6/6 | 100 |
| 2.5 | 6/6 | 100 |
| 5 | 6/6 | 100 |

*Mice were injected intravenously, once within 10 minutes after and once 5 hours after infection. Anti-infective agents were administered in 0.1 ml/mouse/treatment of 5% dextrose for injection.

As shown in Table 3b, variant molecule His27Lys was highly active against *Streptococcus pneumoniae* infection in mice.

TABLE 3c

Efficacy of a variant nisin molecule, His27Lys-His31Lys,
against *Streptococcus pneumoniae* septicemia in mice

| His27Lys-His31Lys (mg/kg/dose)* | Survivors/total | (%) |
|---|---|---|
| 0 | 1/6 | 17 |
| 0.625 | 5/6 | 83 |
| 1.25 | 6/6 | 100 |
| 2.5 | 6/6 | 100 |

*Mice were injected intravenously, once within 10 minutes after and once 5 hours after infection. Anti-infective agents were administered in 0.1 ml/mouse/treatment of 5% dextrose for injection.

As shown in Table 3c, variant molecule His27Lys-His31Lys was highly active against *Streptococcus pneumoniae* infection in mice.

Example 4 demonstrates that variant peptide molecules, containing lysine in place of histidine at position 27 of the mature nisin peptide, or containing lysine in place of histidine at both positions 27 and 31 of the peptide, are active against staphylococcal and streptococcal infections in an animal infection model.

EXAMPLE 5

Efficacy of nisin s.c. against *S. pneumoniae* infection in mice.

These experiments were performed as described in Example 2 above. The results are shown in Tables 4a and 4b below.

TABLE 4a

Efficacy of subcutaneous nisin against *Streptococcus pneumoniae*:
as compared to Vancomycin

| Agent | Treatment (mg/kg/dose*) | Survivors/total | (%) |
|---|---|---|---|
| none | 0 | 1/5 | 20 |
| nisin | 4 | 4/5 | 80 |
| nisin | 8 | 5/5 | 100 |
| nisin | 16 | 5/5 | 100 |
| vancomycin | 2 | 3/5 | 60 |
| vancomycin | 4 | 3/5 | 60 |

*Mice were injected subcutaneously, once within 10 minutes after and once 5 h after infection (inoculum ca $10^3$). Anti-infective agents were administered in 0.2 ml/mouse/treatment of 5% dextrose for injection.

As shown in Table 4a, nisin, administered s.c. at 4 mg/kg/injection was 80% efficacious in preventing the death of mice and was 100% efficacious at higher dosages. In comparison, dosages of 2–4 mg/kg/injection of vancomycin were only 60% efficacious.

Lower dosages of nisin were also tested by the subcutaneous route.

TABLE 4b

Efficacy of low-dose s.c. nisin against *Streptococcus pneumoniae*.

| Nisin (mg/kg/dose)* | Survivors/total | (%) |
|---|---|---|
| 0 | 0/6 | 17 |
| 0.625 | 5/6 | 83 |
| 1.25 | 5/6 | 83 |
| 2.5 | 6/6 | 100 |
| 5 | 6/6 | 100 |

*Mice were injected subcutaneously, once within 10 minutes after and once 5 hours after infection. Anti-infective agents were administered in 0.2 ml/mouse/treatment of 5% dextrose for injection.

As shown in Table 4b, dosages of nisin as low as 2.5 mg/kg/treatment s.c. were 100% efficacious in preventing death of infected animals, and dosages as low as 0.625 mg/kg/treatment protected 83% of animals.

I claim:

1. A method for preventing or treating infection by antibiotic-resistant or multidrug-resistant pathogenic bacterial strains of *Streptococcus pneumoniae*, which comprises administering to a mammal in need of such treatment an effective amount of a lanthocin antimicrobial in excess of its minimal inhibitory concentration wherein the lanthocin is selected from the group consisting of nisin, subtilin, epidermin, gallidermin and pep 5.

2. A method according to claim 1, wherein the lanthocin antimicrobial is administered by subcutaneous injection.

3. A method for preventing or treating infection by antibiotic-resistant or multidrug-resistant pathogenic bacterial strains of *Streptococcus pneumoniae*, which comprises administering to a mammal in need of such treatment an effective amount of a nisin analog, in excess of its minimal inhibitory concentration, and wherein the analog differs from native nisin by 1 or 2 amino acid substitutions.

4. A method according to claim 3, wherein the nisin analog is administered by subcutaneous injection.

5. A method according to any one of claims 1, 2, 3 and 4, wherein the antimicrobial is administered in an amount ranging from about 0.078 mg/kg/dose to about 20 mg/kg/dose.

6. A method according to claim 5 wherein the antimicrobial is administered in an amount ranging from about 0.625 mg/kg/dose to about 10 mg/kg/dose.

* * * * *